US011523896B2

(12) United States Patent
Waltz

(10) Patent No.: US 11,523,896 B2
(45) Date of Patent: Dec. 13, 2022

(54) OCULAR PROTECTION RING

(71) Applicant: Kevin L. Waltz, Indianapolis, IN (US)

(72) Inventor: Kevin L. Waltz, Indianapolis, IN (US)

( * ) Notice: Subject to any disclaimer, the term of this patent is extended or adjusted under 35 U.S.C. 154(b) by 196 days.

(21) Appl. No.: 16/401,309

(22) Filed: May 2, 2019

(65) Prior Publication Data

US 2020/0345478 A1 Nov. 5, 2020

(51) Int. Cl.
*A61F 2/14* (2006.01)
*A61F 9/007* (2006.01)

(52) U.S. Cl.
CPC ............ *A61F 2/14* (2013.01); *A61F 9/00709* (2013.01); *A61F 9/00736* (2013.01)

(58) Field of Classification Search
CPC .. A61F 2/14; A61F 2/147; A61F 2/148; A61F 2/1662; A61F 2/167; A61F 2002/16902; A61F 2/1694; A61F 2220/0008; A61F 2230/0008; A61F 2230/0065; A61F 2230/0076; A61F 2250/001; A61F 2250/0059; A61F 2250/0069; A61F 2250/00736

See application file for complete search history.

(56) References Cited

U.S. PATENT DOCUMENTS

| | | | |
|---|---|---|---|
| 5,267,553 A | * | 12/1993 | Graether ................ A61F 9/007 600/236 |
| 5,374,272 A | | 12/1994 | Arpa et al. |
| 6,068,643 A | * | 5/2000 | Milverton .......... A61B 17/0231 606/107 |
| 6,220,246 B1 | | 4/2001 | Chandler et al. |
| 6,569,153 B1 | | 5/2003 | LaHaye |
| 6,620,098 B1 | | 9/2003 | Milverton |
| 6,685,663 B2 | | 2/2004 | Feinsod |

(Continued)

FOREIGN PATENT DOCUMENTS

WO 2018227014 A1 12/2018
WO 2019040836 A1 2/2019

OTHER PUBLICATIONS

International Search Report and Written Opinion in PCT/US20/31316, International Searching Authority, dated May 4, 2020, pp. 1-14.

(Continued)

*Primary Examiner* — Paul B Prebilic
(74) *Attorney, Agent, or Firm* — Ice Miller LLP

(57) ABSTRACT

A device for reducing the incidence of surgical debris migration within a mammalian eye comprising an anterior portion, the anterior portion with an anterior inner surface and an opposing anterior outer surface, the anterior inner surface and the anterior outer surface terminating at an anterior edge that defines an open anterior end; and a posterior portion, with a posterior inner surface and an opposing posterior outer surface, the posterior inner surface and the posterior outer surface terminating at a posterior edge, the posterior edge defining an open posterior end; and a waist connecting the anterior portion and the posterior portion, the waist comprising a waist inner surface and an opposing waist outer surface; and an aperture extending from the open anterior end, through the waist, and to the open posterior end, the aperture bounded by the anterior inner surface, the waist inner surface, and the posterior inner surface.

16 Claims, 13 Drawing Sheets

(56) References Cited

U.S. PATENT DOCUMENTS

| | | | |
|---|---|---|---|
| 7,001,426 B2 | 2/2006 | Lee et al. | |
| 7,806,929 B2 * | 10/2010 | Brown | A61F 2/1602 623/6.39 |
| 8,496,583 B1 | 7/2013 | Reynard | |
| 8,721,654 B2 | 5/2014 | Page | |
| 10,111,746 B2 | 10/2018 | Wortz et al. | |
| 10,136,989 B2 | 11/2018 | Wortz | |
| 11,395,761 B2 * | 7/2022 | Clarke | A61B 17/0231 |
| 2003/0092970 A1 | 5/2003 | Lee | |
| 2014/0364870 A1 | 12/2014 | Alvarez et al. | |
| 2017/0049429 A1 | 2/2017 | Nallakrishnan | |
| 2017/0143636 A1 | 5/2017 | Jarrett et al. | |
| 2018/0310929 A1 | 11/2018 | Girard et al. | |

OTHER PUBLICATIONS

Kim, D. Brian, MD, What Are Your Top Pearls for Handling Posterior Capsular Rupture? Preoperative planning can help surgeons get through these challenging cases., Cataract & Refiactive Surgery Today Europe, Oct. 2018 pp. 38-44.

Chakrabarti, Arup and Nazm, Nazneen, Posterior Capsular Rent: Prevention and Management, Indian Journal of Ophthalmology, Dec. 2017, pp. 1359-1369, vol. 65(12).

Chang, David F., MD, Managing the Broken Posterior Capsule, Chapter 6, 2013.

Lal, Harbansh, MD, Management of Posterior Capsular Tear, Booklet, Apr. 5, 2019.

International Bureau, International Preliminary Report on Patentability issued in PCT/US2020/031316, dated Nov. 11, 2021, pp. 1-8.

* cited by examiner

FIG. 1-Prior Art

OCULAR PROTECTION RING

BACKGROUND

A cataract is a medical condition in which the lens of a patient's eye hardens and becomes cloudy, resulting in impaired vision. Patients with cataracts seek out cataract surgery to correct their impaired vision. During cataract surgery, the cataract itself is destroyed by phacoemulsification or other means, which carves the cataract into tiny pieces. Surgical debris, consisting of pieces of the cataract, is produced. Various devices are used in phacoemulsification or other means of destruction of the cataract. Debris that remains in the anterior chamber and the lens capsule of the eye can be removed by the surgeon during cataract surgery. Any excess debris in the anterior chamber of the eye is disposed of by the body. Debris can also migrate from the front of the eye to the back of the eye during and after surgery.

In the human eye, a space exists between the anterior surface of the lens capsule and the posterior surface of the iris. When the cataract is destroyed during cataract surgery, inevitably some debris will flow through this space. Debris which flows through this space may then migrate into the vitreous body and is free to migrate throughout the posterior chamber of the eye, including into Berger's space behind the posterior capsule and into the hyaloid canal. Debris in the posterior portion of the eye cannot be removed by the surgeon during surgery. This debris will ultimately be removed by the body naturally, but the process can take weeks or months. Debris settling in the posterior chamber of the eye causes inflammation, which leads to increased recovery time, discomfort, and further impaired vision. This increased recovery time may require application of eye drops, anti-inflammatories, or other drugs at an increased cost to and inconvenience to patients. It may not be possible to control the induced inflammation with drops and stronger medications may be required, including oral medications and injections into the eye. With current practices, surgeons are unable to control the migration of debris resulting from cataract surgery, and they are unable to remove debris once it migrates into the posterior chamber of the eye. Physicians may note the migration of debris to the back of the eye during surgery, but they do not have a readily available solution.

SUMMARY

The present disclosure includes disclosure of a device for reducing the incidence of surgical debris migration within a mammalian eye and a method for conducting cataract surgery. In at least one embodiment, such a device comprises an anterior portion, the anterior portion comprises an anterior inner surface and an opposing anterior outer surface, the anterior inner surface and the anterior outer surface terminate at an anterior edge, the anterior edge defines an open anterior end; and a posterior portion, the posterior portion comprises a posterior inner surface and an opposing posterior outer surface, the posterior inner surface and the posterior outer surface terminate at a posterior edge, the posterior edge defines an open posterior end; and a waist connecting the anterior portion and the posterior portion, the waist comprises a waist inner surface and an opposing waist outer surface; and an aperture extending from the open anterior end, through the waist, and to the open posterior end, the aperture bounded by the anterior inner surface, the waist inner surface, and the posterior inner surface. In an aspect of such an embodiment, such a device is a singular unit constructed of silicone, nylon, or other suitable material. In an aspect of such an embodiment, the circumference of the waist of such a device is less than the circumference of the anterior edge and the posterior edge. In an aspect of such an embodiment, the posterior edge and the anterior edge comprise a regular ellipse or an irregular ellipse. In an aspect of such an embodiment, the anterior portion comprises a straight line or a curve between the waist and the anterior edge. In an aspect of such an embodiment, the posterior portion comprises a straight line or a curve between the waist and the posterior edge. In an aspect of such an embodiment, the mammalian eye comprises a pupil, and such a device is configured to fit within the pupil. In an aspect of such an embodiment, the mammalian eye further comprises an iris and a lens capsule and the waist is configured to engage the lens and the iris.

In at least one embodiment, such a device comprises an anterior portion, the anterior portion comprises an anterior inner surface and an opposing anterior outer surface, the anterior inner surface and the anterior outer surface terminate at an anterior edge, the anterior edge defines an open anterior end; and a posterior portion, the posterior portion comprises a posterior inner surface and an opposing posterior outer surface, the posterior inner surface and the posterior outer surface terminate at a posterior edge, the posterior edge defines an open posterior end; and a waist connecting the anterior portion and the posterior portion, the waist comprises a waist inner surface and an opposing waist outer surface; and an aperture extending from the open anterior end, through the waist, and to the open posterior end, the aperture incompletely bounded by the anterior inner surface, the waist inner surface, and the posterior inner surface; and a gap, the gap divides the anterior portion, the posterior portion, and the waist. In an aspect of such an embodiment, such a device is a singular unit constructed of silicone, nylon, or other suitable material. In an aspect of such an embodiment, the circumference of the waist of such a device is less than the circumference of the anterior edge and the posterior edge. In an aspect of such an embodiment, the posterior edge and the anterior edge comprise a regular ellipse or an irregular ellipse. In an aspect of such an embodiment, the anterior portion comprises a straight line or a curve between the waist and the anterior edge. In an aspect of such an embodiment, the posterior portion comprises a straight line or a curve between the waist and the posterior edge. In an aspect of such an embodiment, the mammalian eye comprises a pupil, and such a device is configured to fit within the pupil. In an aspect of such an embodiment, the mammalian eye further comprises an iris and a lens capsule and the waist is configured to engage the lens and the iris. In an aspect of such an embodiment, such a device comprises fasteners connected to the anterior portion and the posterior portion, the fasteners configured to extend into the gap. In an aspect of such an embodiment, the fasteners comprise surgical sutures, thread, or other suitable fastening material.

In at least one embodiment, such a method for conducting cataract surgery on a mammalian eye, the mammalian eye comprises a pupil, a cornea, a lens capsule, an anterior chamber, and a cataract, said method comprises the steps of dilating the pupil; opening the mammalian eye; creating an incision in the cornea; opening the lens capsule; loosening the cataract in the lens capsule; inserting a device into the mammalian eye, the device comprises an anterior portion, the anterior portion comprises an anterior inner surface and an opposing anterior outer surface, the anterior inner surface and the anterior outer surface terminate at an anterior edge, the anterior edge defines an open anterior end; and a posterior portion, the posterior portion comprises a posterior inner surface and an opposing posterior outer surface, the posterior inner surface and the posterior outer surface terminate at a posterior edge, the posterior edge defines an open posterior end; and a waist connecting the anterior portion and the posterior portion, the waist comprises a waist inner surface and an opposing waist outer surface; and an aperture extending from the open anterior end, through the waist, and to the open posterior end, the aperture bounded by the anterior inner surface, the waist inner surface, and the posterior inner surface; breaking the cataract into small pieces of debris; removing the small pieces of debris; removing the device; and inserting a replacement lens. In an aspect of such an embodiment, the waist of such a device is configured to engage the lens capsule and the iris such that the posterior portion extends into the lens capsule and the anterior portion extends into the anterior chamber.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

Figure 1:
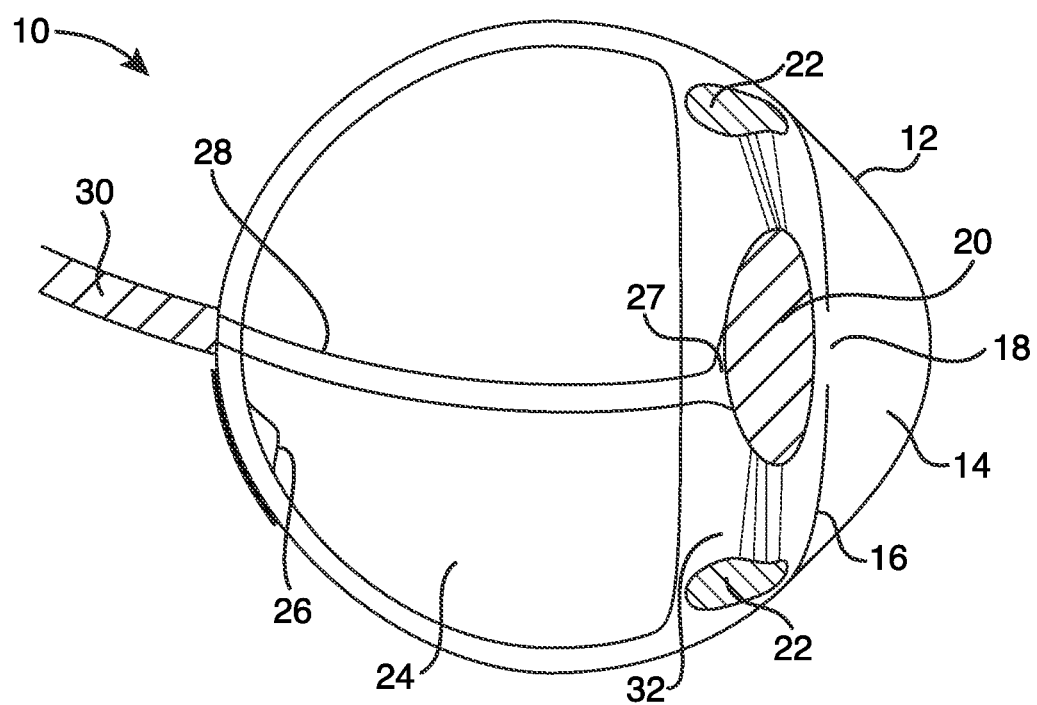
FIG. 1 shows a cross-sectional view of a patient's eye.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 shows a cross-sectional view of a patient's eye 10. The relevant portions of the anterior chamber 14 of the eye 10 are the cornea 12, the iris 16, and the pupil 18. Within the posterior chamber 32 exists the ciliary bodies 22 and the lens capsule 20. The vitreous 24 includes the hyaloid canal 28 and Berger's space 27, located behind the lens capsule 20 and at the anterior extent of the hyaloid canal 28. At the posterior of the eye 10, exists the fovea 26 and the optic nerve 30.

Figure 2:
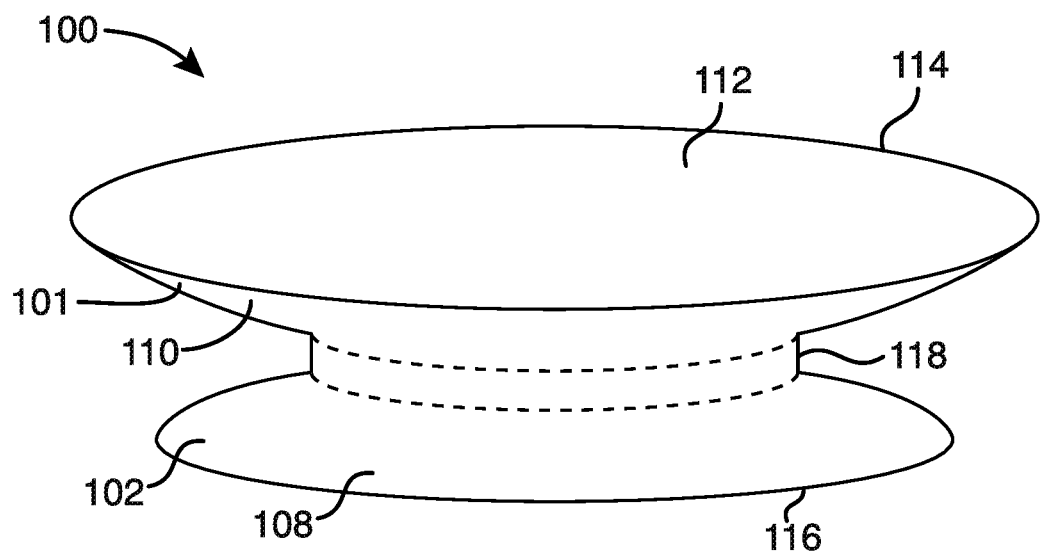
FIG. 2 shows a perspective view of an ocular protection ring according to at least one embodiment of the present disclosure.

FIG. 2 shows a perspective view of an ocular protection ring 100 according to at least one embodiment of the present disclosure. An ocular protection ring 100 according to an embodiment of the present disclosure can be used by surgeons or other medical professionals to protect a patient's eye 10 during various types of eye related surgery, such as cataract surgery, lens replacement surgery, and the like. As described herein, an ocular protection ring 100 of the present disclosure is configured to fit inside of a patient's eye 10 to prevent the passage of surgical debris into the posterior chamber 32, the vitreous 24, or any other portion of the eye 10 that the surgeon or other medical professionals wish to keep reasonably free from surgical debris when performing various eye related surgeries.

As shown in FIG. 2, an ocular protection ring 100 according to at least one embodiment of the present disclosure includes an anterior portion 101 and a posterior portion 102. The anterior portion 101 includes an anterior outer surface 110, an anterior inner surface 112 and an anterior edge 114. The posterior portion 102 includes a posterior outer surface 108, a posterior inner surface 106 and a posterior edge 116. According to an embodiment of the present disclosure the ocular protection ring 100 includes a waist 118 connecting the anterior portion 101 and the posterior portion 102.

According to an embodiment of the present disclosure, the ocular protection ring 100 is constructed as a single piece of silicone, nylon, or other biocompatible material. According to an embodiment of the present disclosure, the waist 118 of the ocular protection ring 100 is sized to fit within anterior capusulotomy, which is within the pupil 18 of the patient's eye 10.

According to at least one embodiment of the present disclosure, the ocular protection ring 100 is constructed in two or more parts. According to this non-limiting embodiment, the two or more parts are assembled in the eye 10 during optical surgery. According to at least one embodiment of the present disclosure, the posterior portion 102 and the waist 118 may comprise a first part, while the anterior portion 101 comprises a second part. According to at least one embodiment of the present disclosure, the posterior portion 102, the waist 118 and the anterior portion 101 may each comprise individual parts.

In at least one embodiment of the present disclosure the circumference of the waist 118 is less than the circumference of the anterior edge 114 and the posterior edge 116. In at least one embodiment of the present disclosure the waist 118 comprises a point formed at the intersection of the anterior outer surface 110 and the posterior outer surface 108. In another non-limiting embodiment of the present disclosure the waist 118 is rounded along its circumference. In another non-limiting embodiment of the present disclosure the waist 118 is squared so as to form a planar surface along the circumference of the waist 118. In at least one non-limiting embodiment of the present disclosure, the anterior edge 114, the posterior edge 116 and the waist 118 are substantially parallel to one another.

In at least one non-limiting embodiment of the present disclosure, the diameter of the waist 118 is less than 4.0 millimeters. In another non-limiting embodiment, the diameter of the waist 118 is less than 5 millimeters. In yet another non-limiting embodiment of the present disclosure the diameter of the waist 118 is between 5 and 6 millimeters. In another non-limiting embodiment the diameter of the waist 118 is greater than 6 millimeters. In another non-limiting embodiment, the diameter of the waist 118 is approximately 5.2 millimeters.

According to an embodiment of the present disclosure, the diameter of the anterior edge 114 is greater than 6 millimeters. In another non-limiting embodiment, the diameter of the anterior edge 114 is between 6 millimeters and 12 millimeters. In yet another non-limiting embodiment of the present disclosure the diameter of the anterior edge 114 is between 8 and 10 millimeters. In another non-limiting embodiment the diameter of the anterior edge 114 is between 9 and 10 millimeters. In another non-limiting embodiment, the diameter of the anterior edge 114 is approximately 9.5 millimeters.

According to an embodiment of the present disclosure, the diameter of the waist 118 is less than 4.0 millimeters. In another non-limiting embodiment, the diameter of the waist 118 is less than 5 millimeters. In yet another non-limiting embodiment of the present disclosure the diameter of the waist 118 is between 5 and 6 millimeters. In another non-limiting embodiment the diameter of the waist 118 is greater than 6 millimeters. In another non-limiting embodiment, the diameter of the waist 118 is approximately 5.2 millimeters.

According to an embodiment of the present disclosure, the diameter of the posterior edge 116 is less than 15 millimeters. In another non-limiting embodiment, the diameter of the posterior edge 116 is greater than 5 millimeters. In yet another non-limiting embodiment of the present disclosure the diameter of the posterior edge 116 is between 5 and 15 millimeters. In another non-limiting embodiment, the diameter of the posterior edge 116 is between 5.2 and 9.5 millimeters.

According to at least one embodiment of the present disclosure the inner anterior surface 112 and the exterior anterior surface 110 create a straight line between the anterior edge 114 and the waist 118. In an embodiment the inner anterior surface 112 and the exterior anterior surface 110 are rounded to create a rounded surface between the anterior edge 114 and the waist 118.

According to at least one embodiment of the present disclosure the posterior outer surface 108 creates a straight line between the posterior edge 116 and the waist 118. In an embodiment the posterior outer surface 108 and the posterior inner surface 106 are rounded to create a rounded surface between the anterior edge 114 and the waist 118.

Figure 3:
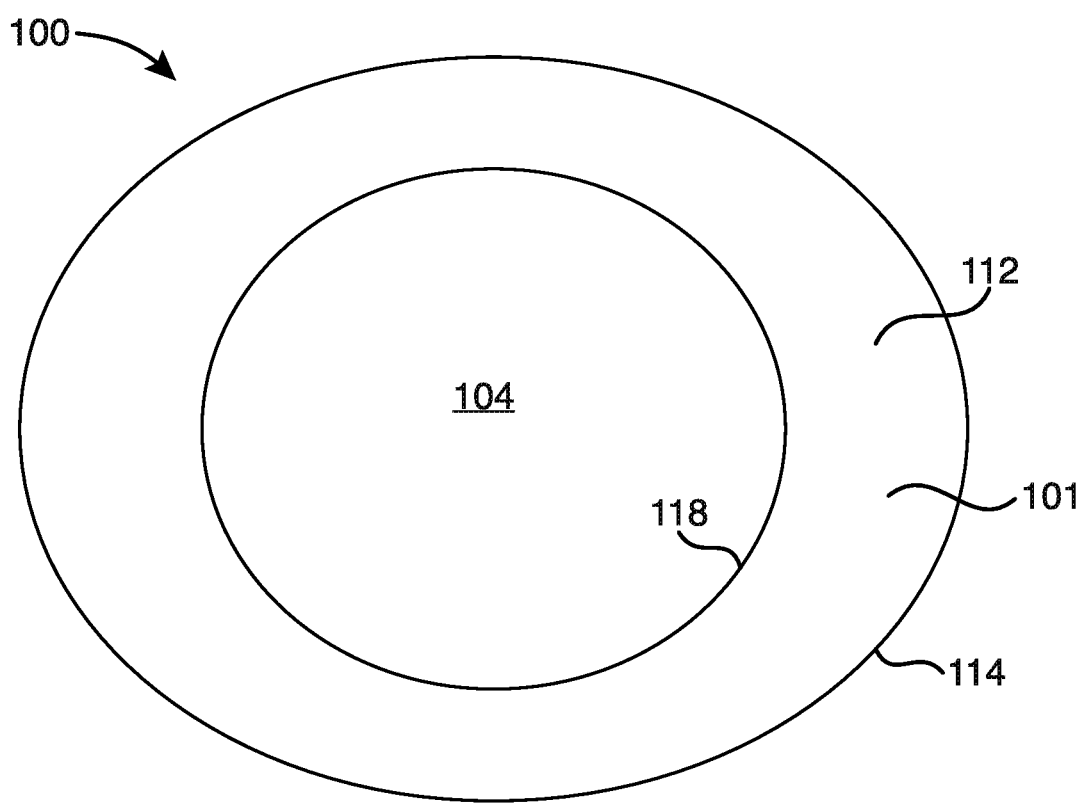
FIG. 3 shows a top view of an ocular protection ring according to at least one embodiment of the present disclosure.

FIG. 3 shows a top view of an ocular protection ring 100 according to at least one embodiment of the present disclosure. Shown in FIG. 3 is the anterior portion 101 of the ocular protection ring 100, including the anterior edge 114 and the anterior inner surface 112. The waist 118 connects the anterior portion 101 and the posterior portion 102. In at least one embodiment of the present disclosure, the ocular protection ring 100 defines an aperture 104.

Figure 4:
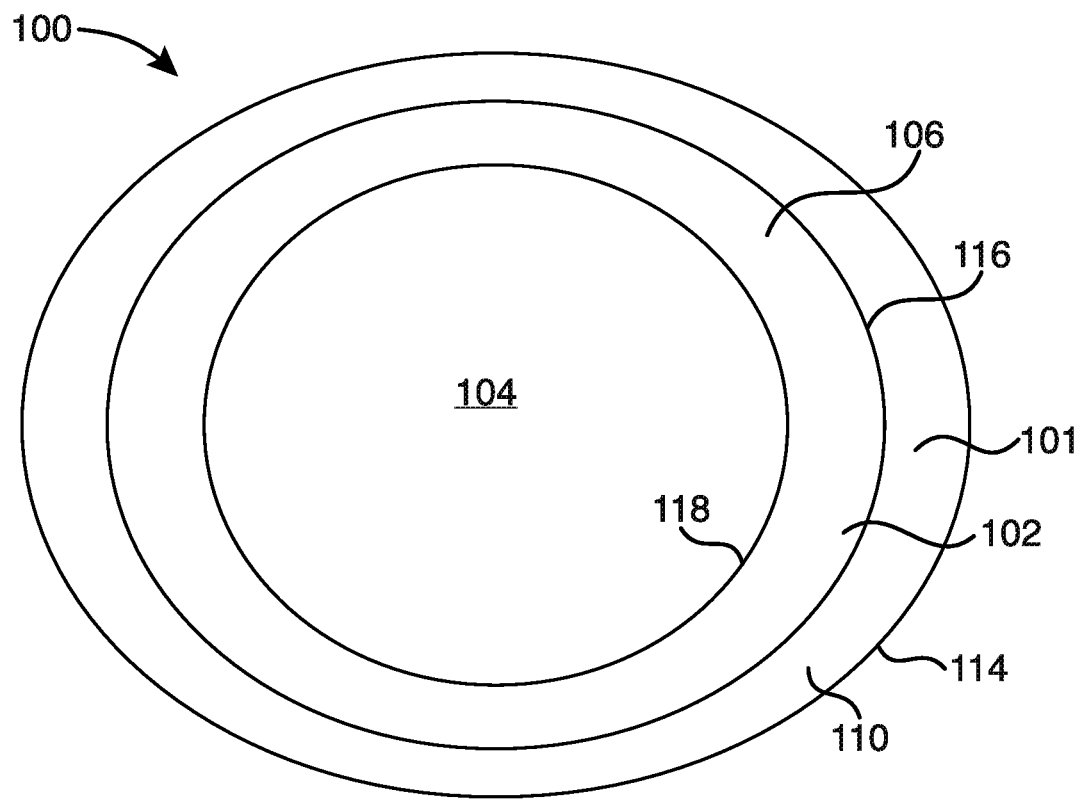
FIG. 4 shows a bottom view of an ocular protection ring according to at least one embodiment of the present disclosure.

FIG. 4 shows a bottom view of an ocular protection ring 100 according to at least one embodiment of the present disclosure. Shown in FIG. 4 is the anterior portion 101, including the anterior edge 114 and the anterior outer surface 110. Also shown is the posterior portion 102, including the posterior inner surface 106 and the posterior edge 116. The waist 118 connects the anterior portion 101 and the posterior portion 102. The aperture 104 is visible, defined by the waist 118.

Figure 5:
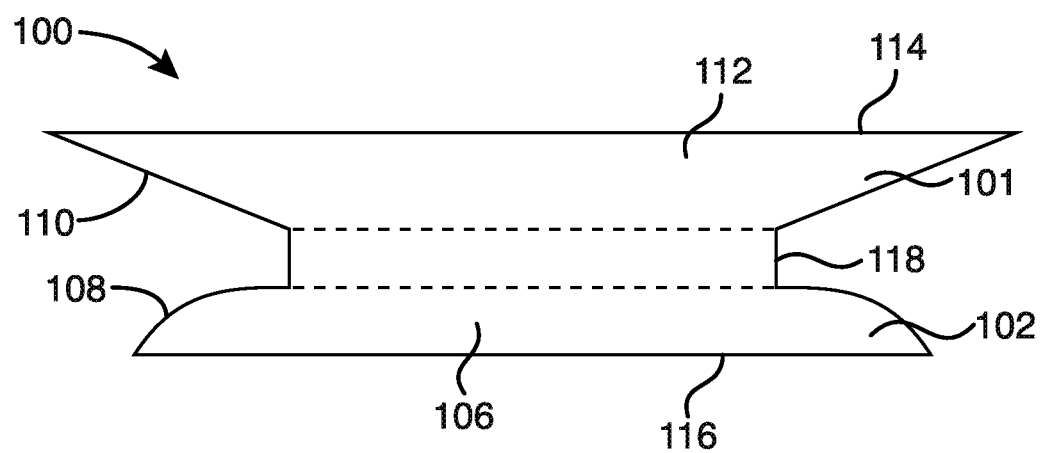
FIG. 5 shows a side view of an ocular protection ring according to at least one embodiment of the present disclosure.

FIG. 5 shows a side view of an ocular protection ring 100 according to at least one embodiment of the present disclosure. Shown in FIG. 5 are anterior portion 101, the posterior portion 102 and the waist 118 connecting the anterior portion 101 and the posterior portion 102. The anterior portion 101 includes the anterior inner surface 112, the anterior outer surface 110, and the anterior edge 114. The posterior portion 101 includes the posterior inner surface 106, the posterior outer surface 108, and the posterior edge 116. FIG. 5 also shows the waist 118 joining the anterior portion 101 to the posterior portion 102.

Figure 6:
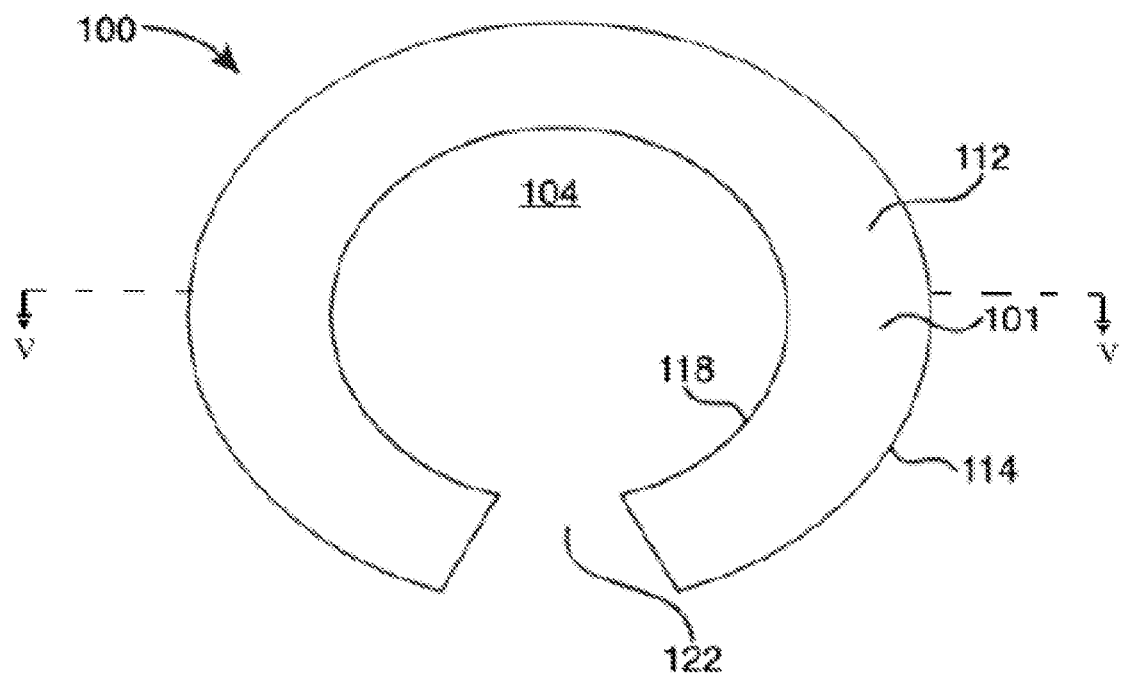
FIG. 6 shows a top view of an ocular protection ring according to at least one embodiment of the present disclosure.

FIG. 6 shows a top view of an ocular protection ring 100 according to at least one embodiment of the present disclosure. According to at least one embodiment of the present disclosure, the ocular protection ring 100 includes an anterior portion 101 and a posterior portion 102. The anterior portion 101 includes an anterior outer surface 110, an anterior inner surface 112 and an anterior edge 114. The posterior portion 102 includes a posterior outer surface 108, a posterior inner surface 106 and a posterior edge 116. According to at least one embodiment of the present disclosure the ocular protection ring 100 includes a waist 118 connecting the anterior portion 101 and the posterior portion 102. According to at least one embodiment of the present disclosure, a gap 122 exists in the ocular protection ring 100 such that the anterior edge 114, the waist 118 and the anterior inner surface 112 do not form a completed ring. In this embodiment, the gap 122 facilitates insertion and placement of the ocular protection ring 100, and the aperture 104 still exists to allow surgery to continue within the lens capsule 20.

Figure 7:
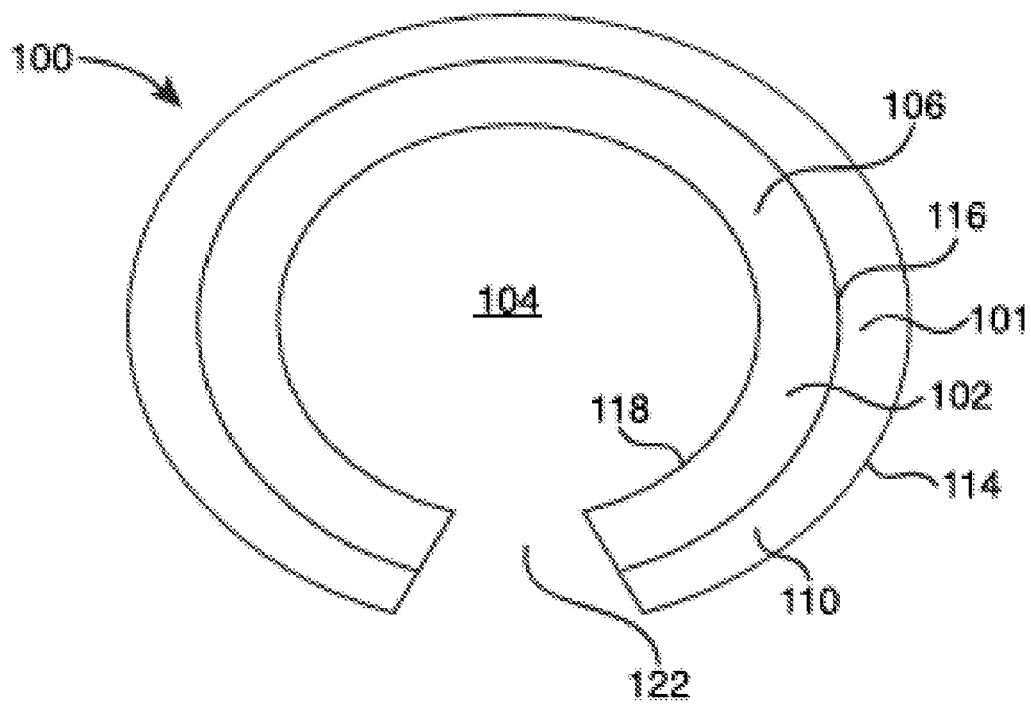
FIG. 7 shows a bottom view of an ocular protection ring according to at least one embodiment of the present disclosure.

FIG. 7 shows a bottom view of the ocular protection ring 100 of FIG. 6 according to at least one embodiment of the present disclosure. Shown in FIG. 7 is the anterior portion 101 of the ocular protection ring 100, including the anterior edge 114 and the anterior inner surface 112. The waist 118 connects the anterior portion 101 and the posterior portion 102. In at least one embodiment of the present disclosure, the ocular protection ring 100 defines an aperture 104. According to at least one embodiment of the present disclosure, a gap 122 exists in the ocular protection ring 100 such that the anterior edge 114, the waist 118 and the posterior edge 116 do not form a completed ring. In this embodiment, the gap 122 facilitates insertion and placement of the ocular protection ring 100, and the aperture 104 still exists to allow surgery to continue within the lens capsule 20.

Figure 8:
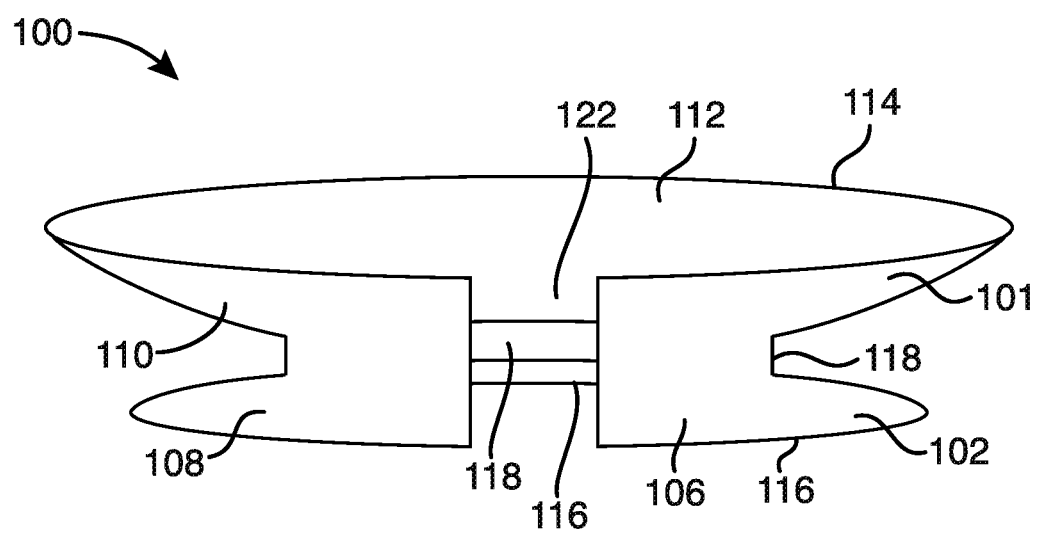
FIG. 8 shows a perspective view of an ocular protection ring according to at least one embodiment of the present disclosure.

FIG. 8 shows a perspective view of the ocular protection ring 100 shown in FIG. 6 according to at least one embodiment of the present disclosure. In this non-limiting embodiment, the anterior edge 114, the waist 118, the posterior edge 106, the posterior outer surface 116 and the anterior outer surface 110 are visible. In this non-limiting embodiment the gap 122 exists in the ocular protection ring 100 such that the anterior edge 114, the waist 118, and the posterior edge 116 do not form a completed ring.

Figure 9:
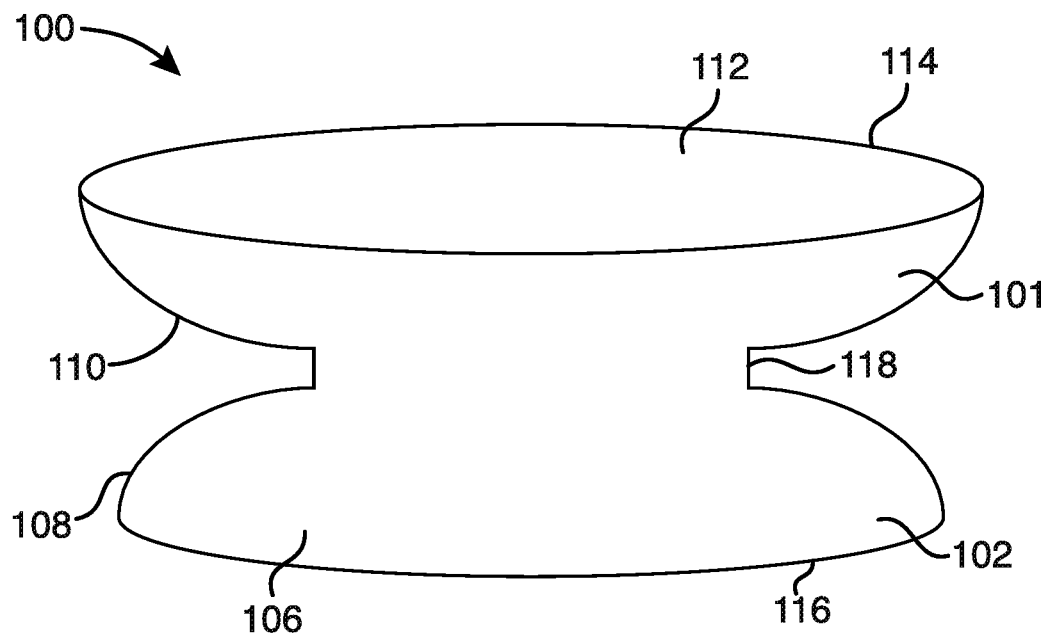
FIG. 9 shows a perspective view of an ocular protection ring according to at least one embodiment of the present disclosure.

FIG. 9 shows a perspective view of an ocular protection ring 100 according to at least one embodiment of the present disclosure. According to this non-limiting embodiment, the posterior outer surface 108 and the anterior outer surface 110 have a curve. According to this non-limiting embodiment, the waist 118 is squared to form nearly a right angle relative to the posterior outer surface 108 and the anterior outer surface 110. In at least one embodiment of the present disclosure the posterior surface 108 is configured to engage smoothly with the inner surface of the lens capsule 20.

Figure 10:
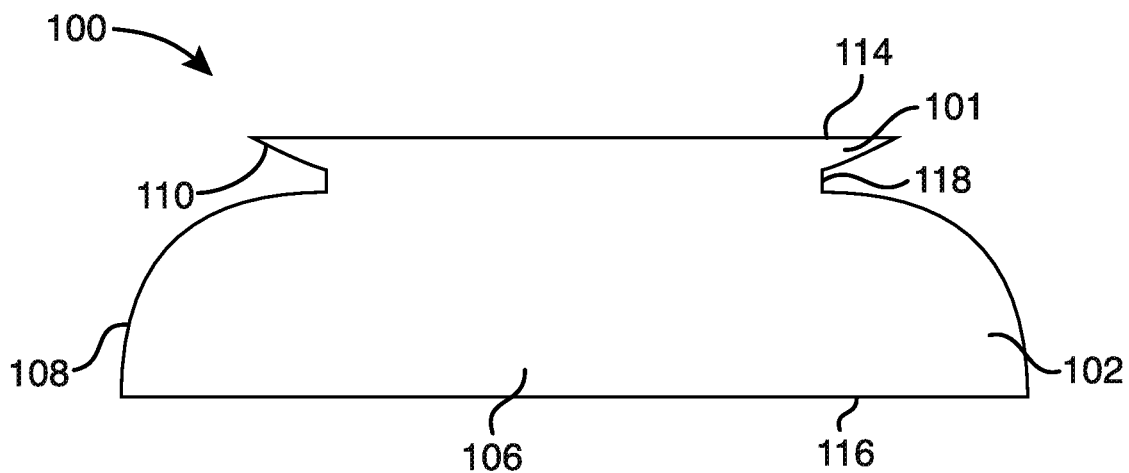
FIG. 10 shows a side view of an ocular protection ring according to at least one embodiment of the present disclosure.

FIG. 10 shows a side view of an ocular protection ring 100 according to at least one embodiment of the present disclosure. According to this non-limiting embodiment, the posterior outer surface 108 is curved, while the anterior outer surface 110 makes a straight line between the waist 118 and the anterior edge 114. According to this non-limiting embodiment, the waist 118 is squared to form nearly a right angle relative to the posterior outer surface 108 and the anterior outer surface 110.

Figure 11:
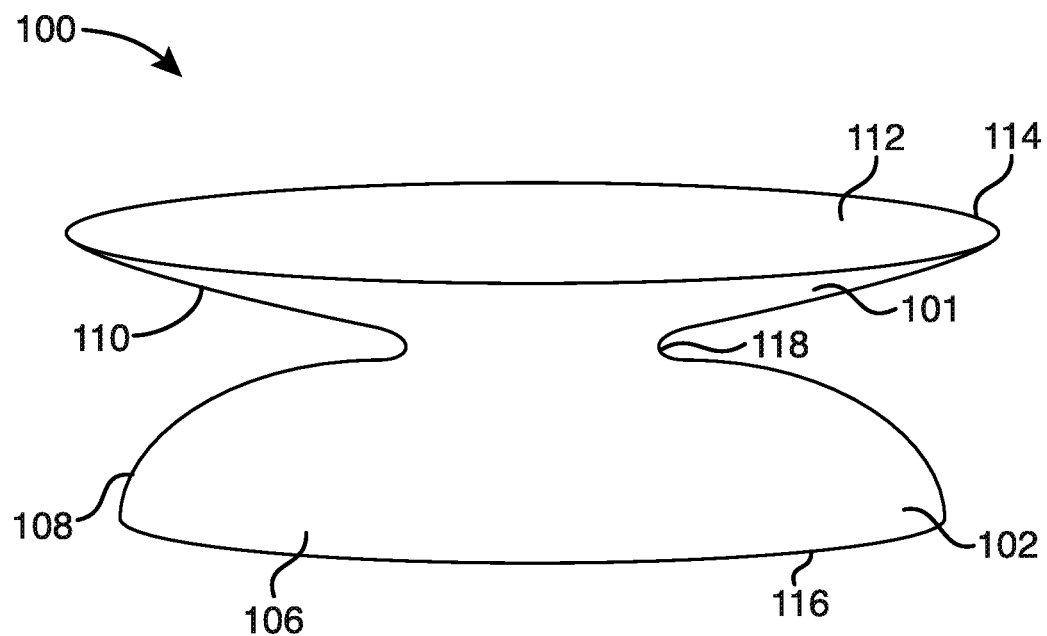
FIG. 11 shows a side view of an ocular protection ring according to at least one embodiment of the present disclosure.

FIG. 11 shows a side view of an ocular protection ring 100 according to at least one embodiment of the present disclosure. In this non-limiting embodiment, the posterior outer surface 108 is curved, while the anterior outer surface 110 forms a straight line between the waist 118 and the anterior edge 114. According to this non-limiting embodiment, the waist 118 is curved.

Figure 12:
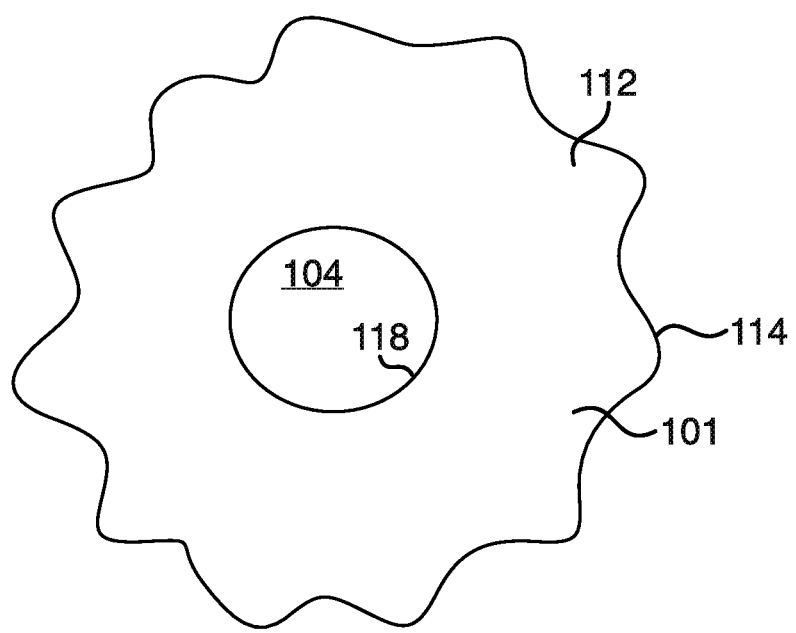
FIG. 12 shows a top view of an ocular protection ring according to at least one embodiment of the present disclosure.

FIG. 12 shows a top view of an ocular protection ring 100 according to at least one embodiment of the present disclosure. According to this non-limiting embodiment, the anterior edge 114 is elliptical and contains a series of waves while the posterior edge 116 is a smooth ellipse.

Figure 13:
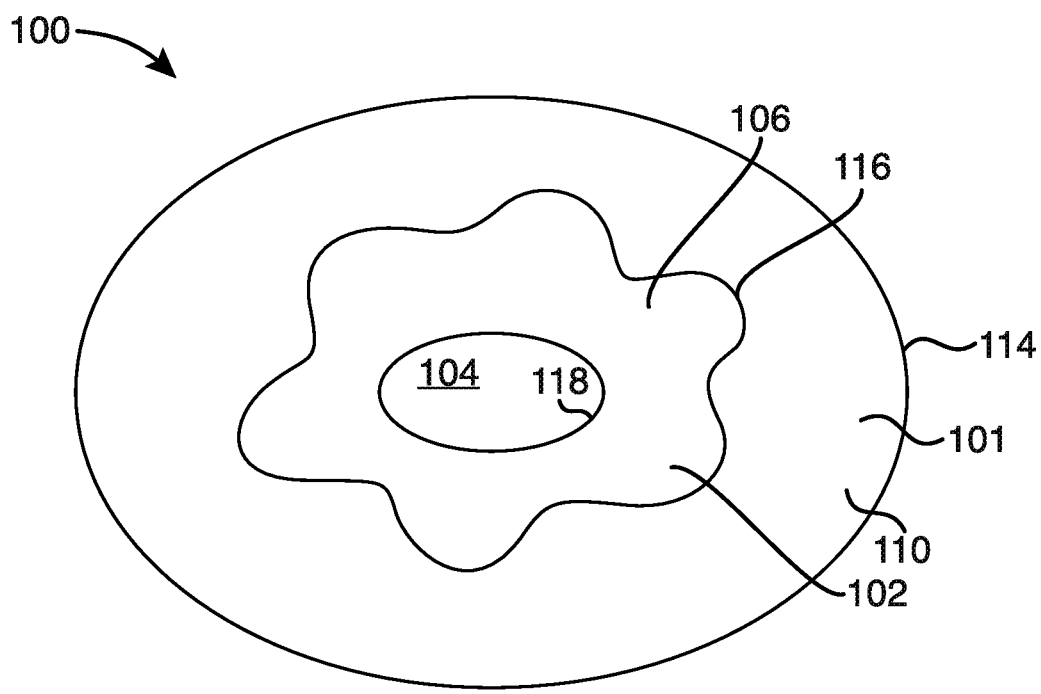
FIG. 13 shows a bottom view of an ocular protection ring according to at least one embodiment of the present disclosure.

FIG. 13 shows a bottom view of an ocular protection ring 100 according to at least one embodiment of the present disclosure. According to this non-limiting embodiment, the anterior edge 114 is a smooth ellipse, while the posterior edge 116 contains a series of waves.

Figure 14:
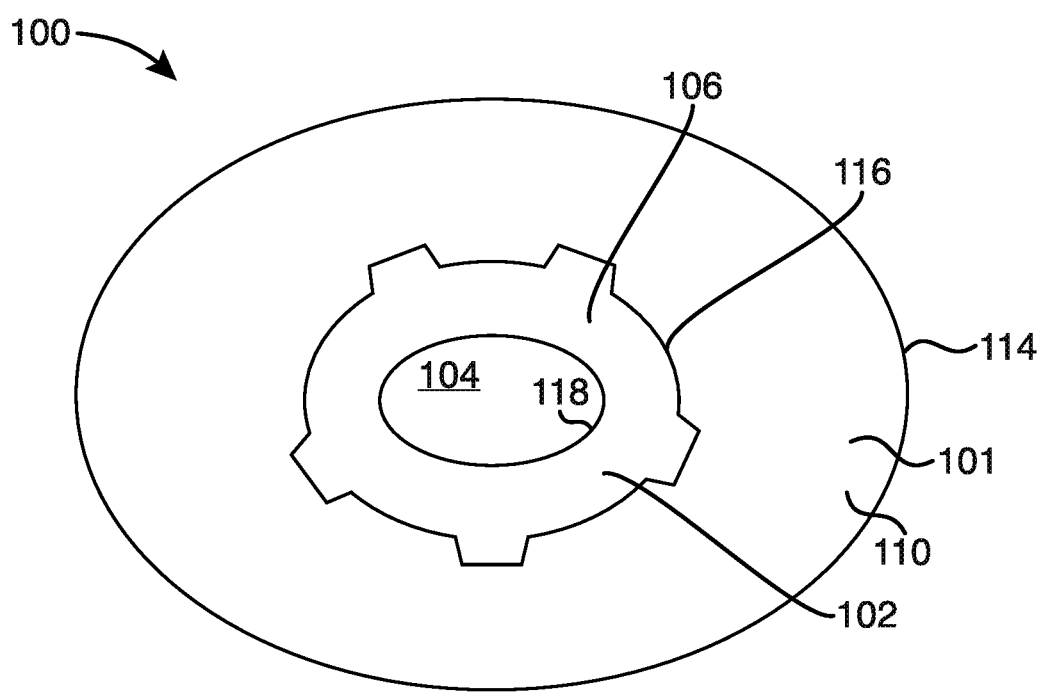
FIG. 14 shows a bottom view of an ocular protection ring according to at least one embodiment of the present disclosure.

FIG. 14 shows a bottom view of an ocular protection ring 100 according to at least one embodiment of the present disclosure. According to this non-limiting embodiment, the anterior edge 114 is a smooth ellipse, while the posterior edge 116 contains a series of outcroppings resembling a gear.

Figure 15:
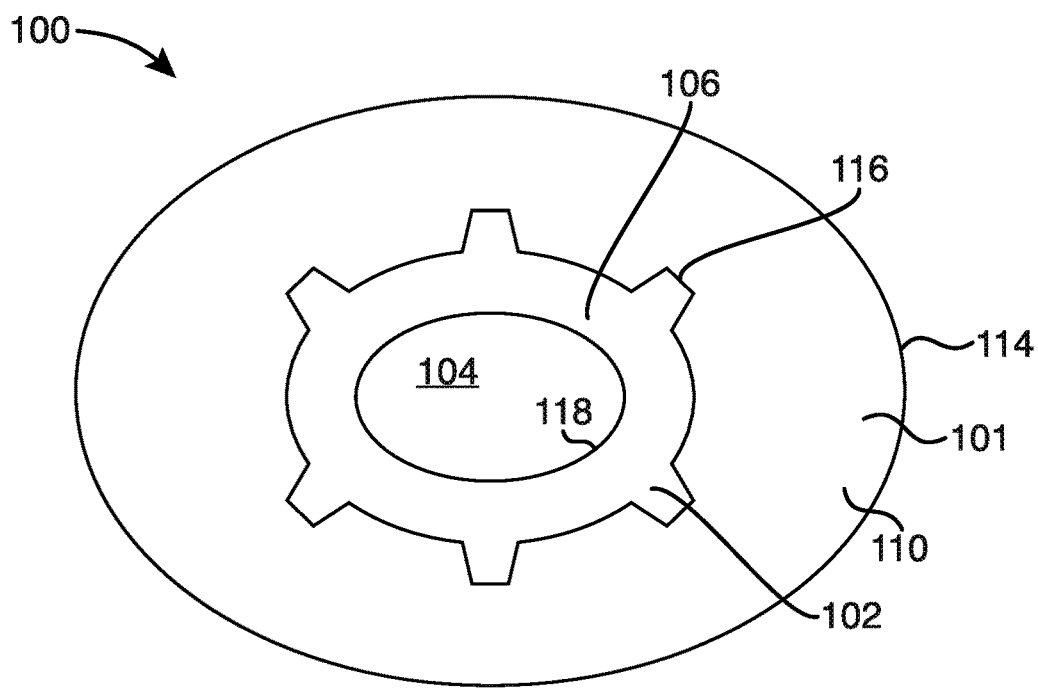
FIG. 15 shows a bottom view of an ocular protection ring according to at least one embodiment of the present disclosure.

FIG. 15 shows a bottom view of an ocular protection ring 100 according to at least one embodiment of the present disclosure. According to this non-limiting embodiment, the anterior edge 114 is a smooth ellipse, while the posterior edge 116 contains a series of outcroppings resembling blades.

Figure 16:
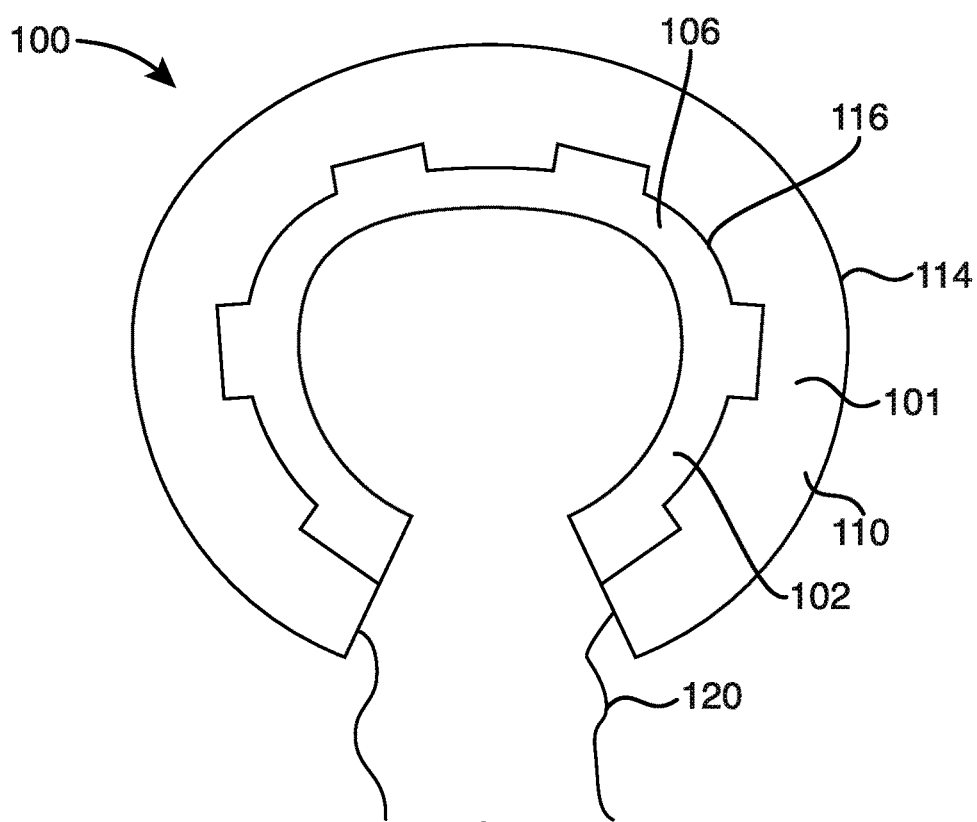
FIG. 16 shows a bottom view of an ocular protection ring according to at least one embodiment of the present disclosure.

FIG. 16 shows a bottom view of an ocular protection ring 100 according to at least one embodiment of the present disclosure. According to this non-limiting embodiment, the ocular protection ring 100 does not form a completed ring. According to this non-limiting embodiment, fasteners 120 extend from the ocular protection ring 100. These fasteners 120 are selected from the group consisting of thread, a suture, or other suitable fastener. According to at least one embodiment of the present disclosure, the fasteners 120 are used to extend through the gap 122 to connect the ends of the ocular protection ring 100. According to at least one embodiment of the present disclosure, the fasteners 120 assist in insertion, placement and removal of the ocular protection ring 100.

Figure 17:
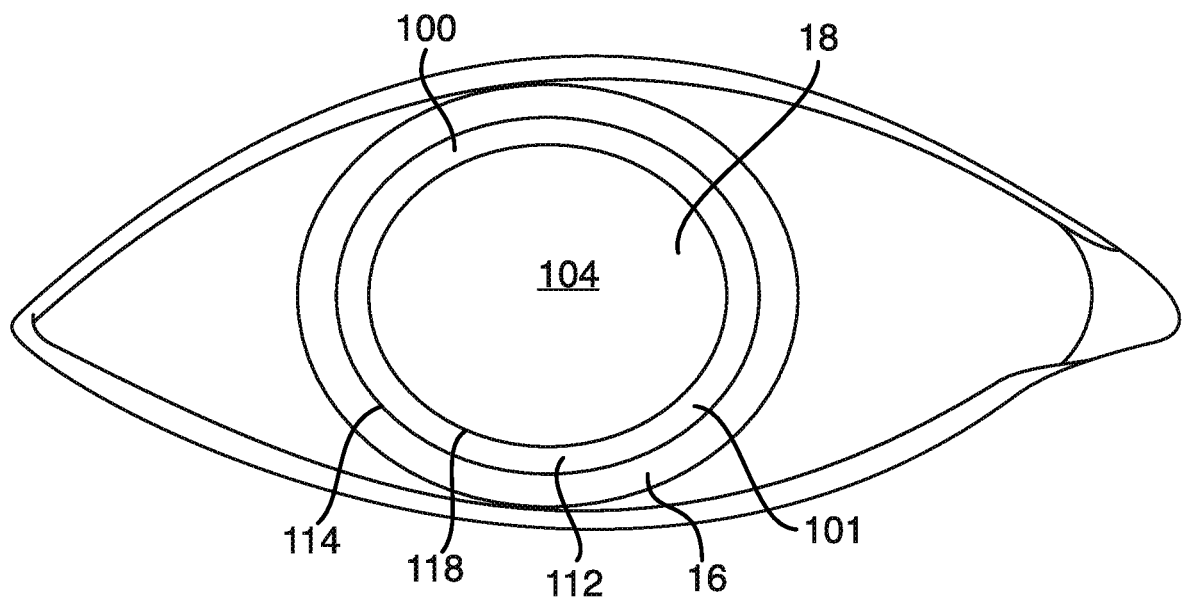
FIG. 17 shows a top view of an ocular protection ring according to at least one embodiment of the present disclosure engaged with a patient's eye.

FIG. 17 shows a top view of an ocular protection ring 100 according to at least one embodiment of the present disclosure engaged with a patient's eye 10. In an embodiment, the waist 118 engages the iris 16 and the lens capsule 20 of a patient's eye 10. According to an embodiment the anterior inner surface 112 and the anterior edge 114 extend anteriorly away from the iris 16 into the anterior chamber 14. According to an embodiment the waist 118 defines the outline of the pupil 18. According to an embodiment the aperture 104 allows vision of the interior of the lens capsule 20.

Figure 18:
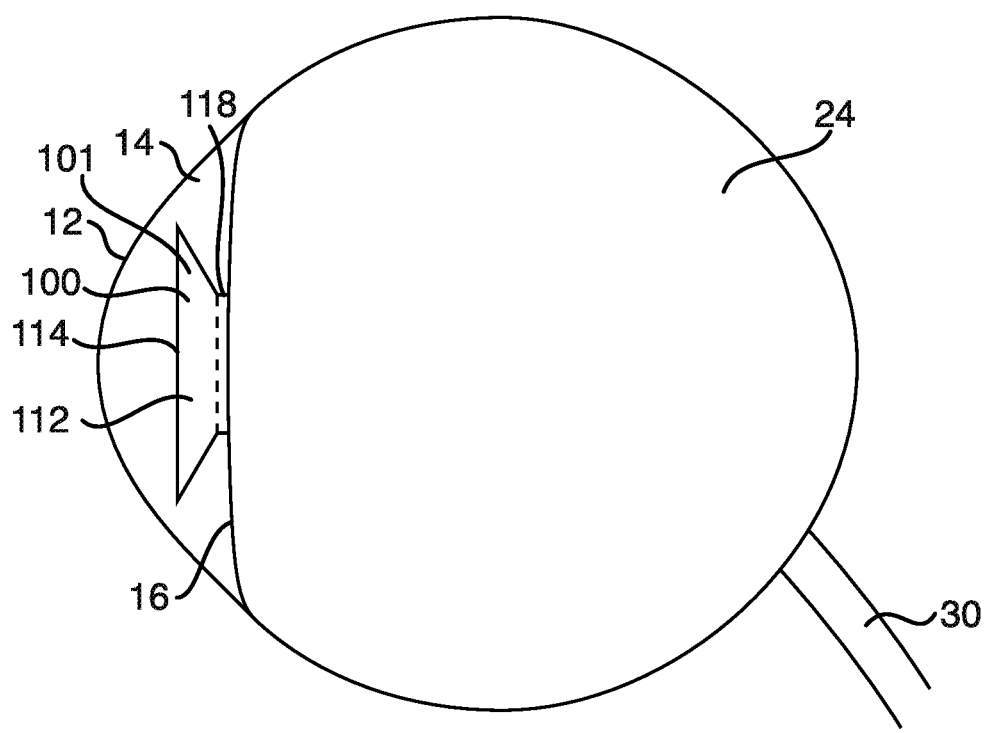
FIG. 18 shows a side view of an ocular protection ring according to at least one embodiment of the present disclosure engaged with a patient's eye.

FIG. 18 shows a side view of an ocular protection ring 100 according to at least one embodiment of the present disclosure engaged with a patient's eye 10. In an embodiment the ocular protection ring 100 is inserted inside the pupil 18 of a patient's eye 10. According to an embodiment of the present disclosure the outer surface of the waist 118 engages the iris 16 and the lens capsule 20. According to an embodiment, when engaged with the eye 10, the anterior outer surface 110, the anterior inner surface 112 and the anterior edge 114 of the ocular protection ring 100 extend into the anterior chamber 14 of the eye 10.

Figure 19:
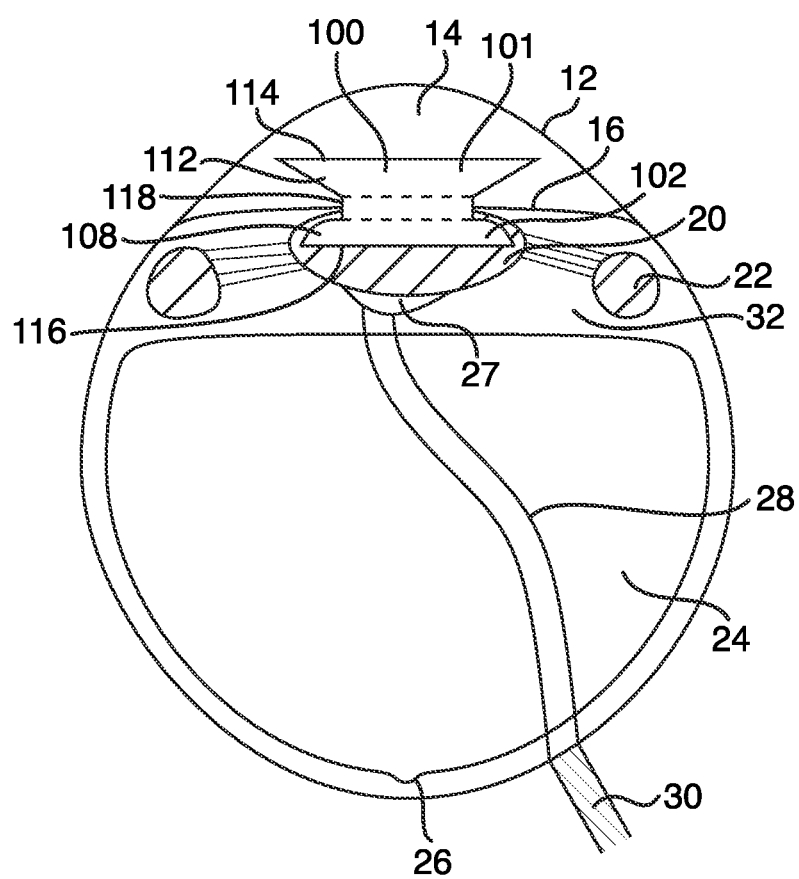
FIG. 19 shows a partial cross-sectional view of an ocular protection ring according to at least one embodiment of the present disclosure engaged with a patient's eye.

FIG. 19 shows a partial cross-sectional view of an ocular protection ring 100 according to at least one embodiment of the present disclosure-engaged with a patient's eye 10. According to an embodiment the waist 118 of the ocular protection ring 100 engages the surface of the iris 16 and the lens capsule 20. According to an embodiment of the present disclosure the outer surface of the waist 118 engages the iris 16 and the lens capsule 20. According to an embodiment, when engaged with the eye 10 the anterior inner surface 112 and the anterior edge 114 of the ocular protection ring 100 extend into the anterior chamber 14 of the eye 10. According to an embodiment, when engaged with the eye 10 the posterior inner surface 106 and the posterior edge 116 of the ocular protection ring 100 are inside of the lens capsule 20 of the eye 10.

Figure 20:
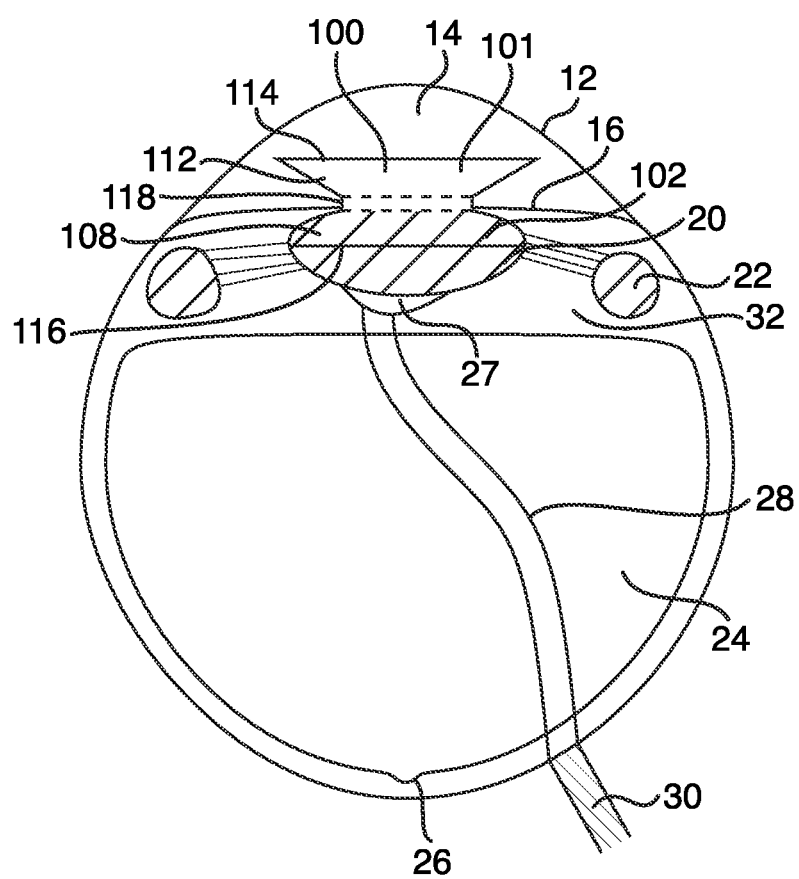
FIG. 20 shows a partial cross-sectional view of an ocular protection ring according to at least one embodiment of the present disclosure engaged with a patient's eye.

FIG. 20 shows a partial cross-sectional view of an ocular protection ring 100 according to at least one embodiment of the present disclosure engaged with a patient's eye 10. According to this non-limiting embodiment, the posterior outer surface 108 conforms to the interior of the lens capsule 20.

According to an embodiment of the present disclosure, the engagement of the waist 118 of the ocular protection ring 100 with the iris 16 and the anterior surface of the lens capsule 20 creates a physical barrier protecting the space between the lower surface of the iris 16 and the upper surface of the lens capsule 20 from the passage of surgical debris or other material. In this embodiment, the waist 118 creates a physical barrier preventing the passage of debris or other material into the posterior chamber 32, the vitreous 24, the hyaloid canal 28 or any other area of the eye. In this embodiment, the waist 118 contains debris within the lens capsule 20 and the anterior chamber 14 of the eye 10. According to at least one embodiment of the present disclosure, the circumference of the waist 118 is less than the circumference of the anterior edge 114 and the posterior edge 116, thereby maintaining engagement of the iris 16 and the anterior surface of the lens capsule 20 with the waist 118.

According to at least one embodiment of the present disclosure, the engagement of the iris 16 and the anterior surface of the lens capsule to the waist 118 of the ocular protection ring 100 maintains surgical debris within the lens capsule 20 and the anterior chamber 14, where it can easily be removed by the surgeon. According to at least one embodiment of the present disclosure, the posterior outer surface 108 is formed to the interior of the lens capsule 20 to strengthen the physical barrier between the anterior surface of the lens capsule 20 and the posterior surface of the iris 16, further closing the posterior chamber to the circulating debris created during removal of the cataract.

According to at least one embodiment of the present disclosure, the anterior exterior surface 112 of the ocular protection ring 100 is formed to the anterior surface of the iris 16, thereby preventing the flow of any surgical debris into the space between the anterior surface of the lens capsule 20 and the iris 16.

According to at least one embodiment of the present disclosure, the anterior edge 114 and the posterior edge 116 are elliptical and contain waves or outcroppings resembling gears or blades. The various shapes of the anterior edge 114 and the posterior edge 116 shown in these embodiments assist in holding the iris 16 in place to prevent the shrinking of the pupil 18 during surgery. The various shapes of the anterior edge 114 and the posterior edge 116 shown in these embodiments also protect the patient from the adverse effects of "floppy iris syndrome", which causes the iris 16 to become fluid during surgery.

Figure 21:
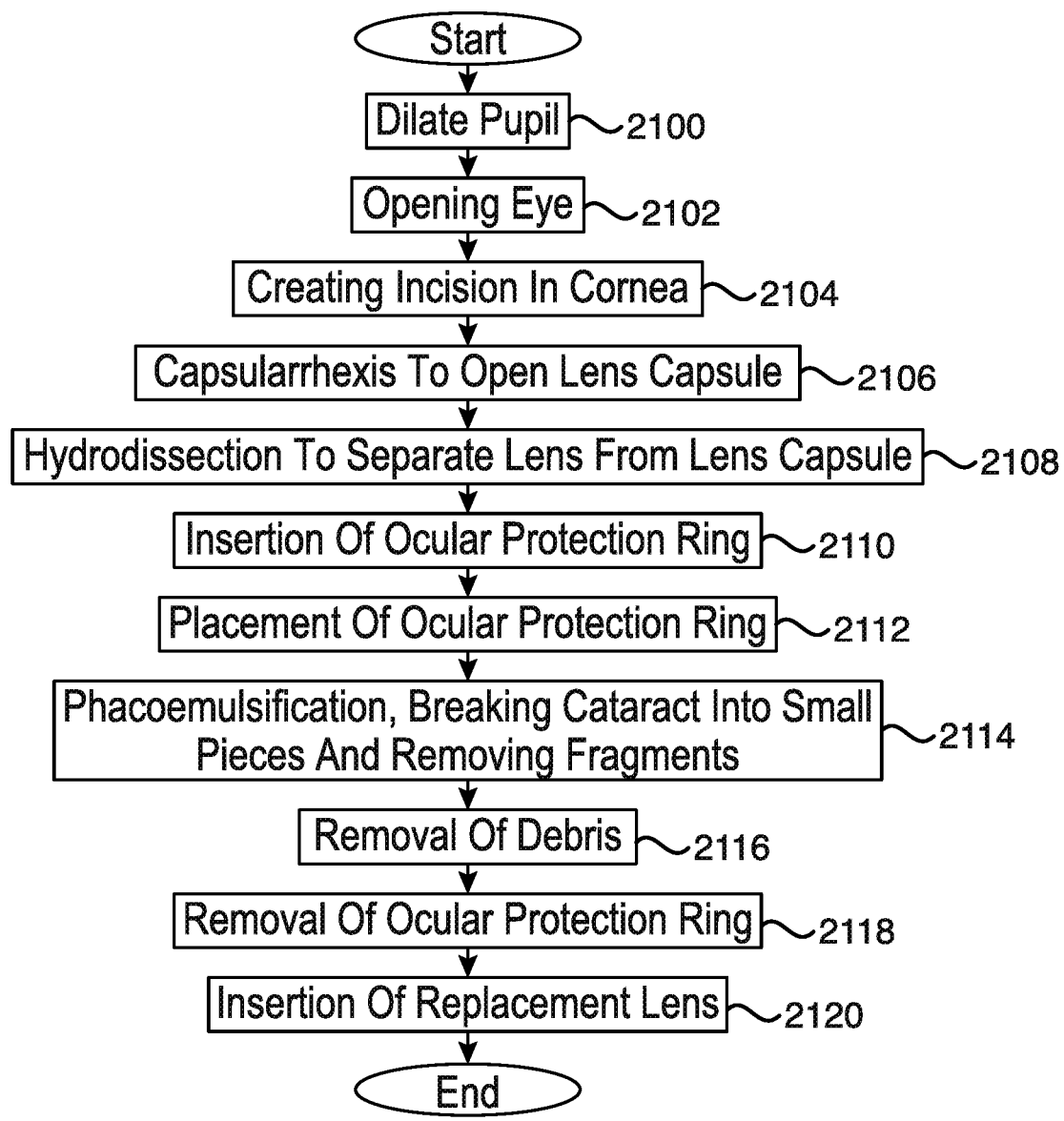
FIG. 21 is a flowchart of a method for inserting and positioning an ocular protection ring in a patient's eye according to at least one embodiment of the present disclosure.

FIG. 21 is a flowchart of a method for inserting and positioning an ocular protection ring 100 in a patient's eye 10 according to at least one embodiment of the present disclosure. According to the present disclosure, block 2100 shows the pupil 18 is dilated. At this step, anesthesia may be applied. Block 2102 shows that the patient's eye 10 opened.

Block 2104 shows that one or more surgical incisions are made in the cornea 16, allowing access to the anterior chamber 14 of the eye 10. A viscoelastic may be injected into the anterior chamber 14 of the eye 10. According to the present disclosure, block 2106 shows that capsulorrhexis is performed, creating an opening in the lens capsule 20, thereby allowing access to the cataract inside the lens capsule 20. According to the present disclosure, the opening in the lens capsule 20 may be elliptical. As shown in block 2110, according to the present disclosure, the surgeon conducts hydrodissection to loosen the cataract within the lens capsule 20. According to an embodiment of the present disclosures, the surgeon may perform hydrodelineation in addition to or as a replacement for hydrodissection. According to the present disclosure, the ocular protection ring 100 is inserted into the eye 10 as shown by block 2110. According to the present disclosure the ocular protection ring 100 is made of a flexible material such that it may be compactly folded to assist with insertion into the eye 10 through small surgical incisions in the cornea 12. According to the present disclosure, the ocular protection ring 100 may be inserted into the eye 10 in multiple parts and assembled within the eye 10. Block 2112 shows that according to the present disclosure, the ocular protection ring 100 is moved into place such that the waist 118 engages the anterior surface of the lens capsule 20 and the iris 16, creating a physical barrier between the iris and the anterior surface of the lens capsule 20. According to the present disclosure, the anterior portion 101 of the ocular protection ring 100, extends into the anterior chamber 14 of the patients eye 10, and the posterior portion 102 extends into the lens capsule 20. Block 2114 shows, according to the present disclosure, phacoemulsification is performed, carving the cataract into small pieces. According to the present disclosure, the ocular protection ring 100 controls the flow of surgical debris and the small pieces of the cataract such that the debris remains within the anterior chamber 14 and the lens capsule 20. These pieces are removed from the eye 10 in block 2116. Block 2118 shows that, according to the present disclosure, after phacoemulsification the ocular protection ring 100 is removed from the patient's eye 10. According to at least one embodiment of the present disclosure the ocular protection ring 100 is disassembled within the eye 10 and removed as separate parts. According to the present disclosure, block 2120 shows that a replacement lens is inserted through the surgical incisions in the cornea 12 and placed in the lens capsule 20 of the patient's eye 10. According to the present disclosure, the viscoelastic is removed and the wounds are sealed.

While this disclosure has been described as having various embodiments, these embodiments according to the present disclosure can be further modified within the scope and spirit of this disclosure. This application is therefore intended to cover any variations, uses, or adaptations of the disclosure using its general principles. For example, any methods disclosed herein represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

What is claimed is:

1. A device for reducing the incidence of surgical debris migration within a mammalian eye comprising a pupil, a cornea, a lens capsule, an iris, and a space between the lens capsule and the iris, the device comprising:
   an anterior portion, said anterior portion comprising an anterior inner surface and an opposing anterior outer surface, said anterior inner surface and said anterior outer surface terminating at an anterior edge, said anterior edge defining an open anterior end;
   a posterior portion, said posterior portion comprising a posterior inner surface and an opposing posterior outer surface, said posterior inner surface and said posterior outer surface terminating at a posterior edge, said posterior edge defining an open posterior end;
   a waist connecting said anterior portion and said posterior portion, said waist comprising a waist inner surface and an opposing waist outer surface; and
   an aperture extending from said open anterior end, through said waist, and to said open posterior end, said aperture bounded by said anterior inner surface, said waist inner surface, and said posterior inner surface;
   wherein said posterior edge and said anterior edge comprise an elliptical shape; and wherein said mammalian eye comprises an iris and a lens capsule and said waist outer surface is structured to conform to an interior of said iris and said posterior outer surface is structured to conform to an interior of said lens capsule;

wherein the device is made of flexible material and is structured to impede the flow of debris through the space between the lens capsule and the iris.

2. The device of claim 1 wherein said device is a singular unit constructed of silicone, nylon, or other biocompatible material.

3. The device of claim 1 wherein said waist is narrower than said anterior edge and said posterior edge.

4. The device of claim 1 wherein said anterior portion comprises a straight line or a curve between said waist and said anterior edge.

5. The device of claim 1 wherein said posterior portion comprises a straight line or a curve between said waist and said posterior edge.

6. The device of claim 1 wherein said mammalian eye comprises a pupil, and said device is configured to fit within said pupil.

7. A device for reducing the incidence of surgical debris migration within a mammalian eye comprising a pupil, a cornea, a lens capsule, an iris, and a space between the lens capsule and the iris, the device comprising:
    an anterior portion, said anterior portion comprising an anterior inner surface and an opposing anterior outer surface, said anterior inner surface and said anterior outer surface terminating at an anterior edge, said anterior edge defining an open anterior end;
    a posterior portion, said posterior portion comprising a posterior inner surface and an opposing posterior outer surface, said posterior inner surface and said posterior outer surface terminating at a posterior edge, said posterior edge defining an open posterior end;
    a waist connecting said anterior portion and said posterior portion, said waist comprising an waist inner surface and an opposing waist outer surface;
    an aperture extending from said open anterior end, through said waist, and to said open posterior end, said aperture incompletely bounded by said anterior inner surface, said waist inner surface, and said posterior inner surface; and
    a gap, said gap dividing said anterior portion, said posterior portion, and said waist;
    wherein said posterior edge and said anterior edge comprise an elliptical shape; and
    wherein said mammalian eye comprises an iris and a lens capsule and said waist outer surface is structured to conform to an interior of said iris and said posterior outer surface is structured to conform to an interior of said lens capsule;
    wherein the device is made of flexible material and is configured to impede the flow of debris through the space between the lens capsule and the iris.

8. The device of claim 7 wherein said device is a singular unit constructed of silicone, nylon, or other biocompatible material.

9. The device of claim 7 wherein said waist is narrower than said anterior edge and said posterior edge.

10. The device of claim 7 wherein said anterior portion comprises a straight line or a curve between said waist and said anterior edge.

11. The device of claim 7 wherein said posterior portion comprises a straight line or a curve between said waist and said posterior edge.

12. The device of claim 7 wherein said mammalian eye comprises a pupil, and said device is configured to fit within said pupil.

13. The device of claim 7 further comprising fasteners connected to said anterior portion and said posterior portion, said fasteners configured to extend into said gap.

14. The device of claim 13 wherein said fasteners comprise surgical sutures, thread, or other fasteners.

15. A method of performing cataract surgery on a mammalian eye, said mammalian eye comprising a pupil, a cornea, a lens capsule, an anterior chamber, a cataract, and a space between the lens capsule and an iris, said method comprising:
    dilating said pupil;
    opening said mammalian eye;
    creating an incision in said cornea;
    opening said lens capsule;
    loosening said cataract in said lens capsule;
    inserting a device into said mammalian eye, the device comprising:
        an anterior portion, said anterior portion comprising an anterior inner surface and an opposing anterior outer surface, said anterior inner surface and said anterior outer surface terminating at an anterior edge, said anterior edge defining an open anterior end,
        a posterior portion, said posterior portion comprising a posterior inner surface and an opposing posterior outer surface, said posterior inner surface and said posterior outer surface terminating at a posterior edge, said posterior edge defining an open posterior end,
        a waist connecting said anterior portion and said posterior portion, said waist comprising a waist inner surface and an opposing waist outer surface, and
        an aperture extending from said open anterior end, through said waist, and to said open posterior end, said aperture bounded by said anterior inner surface, said waist inner surface, and said posterior inner surface;
        wherein once placed, the posterior outer surface conforms to an interior surface of said lens capsule; and
        wherein the device is made of flexible material and is configured to impede the flow of debris through the space between the lens capsule and the iris;
    breaking said cataract into small pieces of debris;
    removing said small pieces of debris;
    removing said device; and
    inserting a replacement lens.

16. The method of claim 15 wherein said waist of said device is configured to engage said lens capsule and said iris such that said posterior portion extends into said lens capsule and said anterior portion extends into said anterior chamber.

* * * * *